United States Patent [19]

Takeya

[11] Patent Number: 5,554,766
[45] Date of Patent: Sep. 10, 1996

[54] PROCESS FOR PREPARING WATER-SOLUBLE ORGANIC OXIDE

[75] Inventor: Haruhiko Takeya, Satte, Japan

[73] Assignees: Cosmo Research Institute; Cosmo Oil Co., Ltd., both of Tokyo, Japan

[21] Appl. No.: 389,201

[22] Filed: Feb. 15, 1995

[30] Foreign Application Priority Data

Feb. 22, 1994 [JP] Japan ................................. 6-023887

[51] Int. Cl.⁶ ............................................. C07C 227/02
[52] U.S. Cl. ........................... 548/473; 548/512; 548/513; 562/567; 562/526
[58] Field of Search .................................. 562/567, 526; 548/473, 512, 513

[56] References Cited

U.S. PATENT DOCUMENTS 5,380,935  1/1995  Takeya et al. ......................... 562/567

FOREIGN PATENT DOCUMENTS 0607952  7/1994  European Pat. Off. .

OTHER PUBLICATIONS

The Journal of The Chemical Society, Section D, vol. 18, pp. 1099–1100, 1971, G. Quistad, et al., "Pyrrole Photo–Oxidation. The Direct Formation Of Maleimides".

Biochemical and Biophysical Research Communications, vol. 78, No. 1, pp. 418–423, 1977, T. Noguchi, et al., "Conversion of 2,5–Dimethylfuran To 2-Hydroxy–5–Hydroperoxy–2, 5–Dimethyldihydrofuran, A True 1O2–Derived Reaction In Aqueous 1O2 Generating Systems".

Heterocycles, vol. 27, No. 3, pp. 599–603, 1988, Yueh-Haiung Kuo, et al., "Two Crystalline Dimeric Peroxides From Sensitized Photooxidation Of 2,5–Dimethylfuran".

*Primary Examiner*—Jacqueline Haley
*Attorney, Agent, or Firm*—Oblon, Spivak, McClelland, Maier, & Neustadt, P.C.

[57] ABSTRACT

A process for preparing a water-soluble organic oxide which comprises reacting an oil-soluble organic compound with molecular oxygen in the presence of a water-insoluble sensitizer in an organic solvent phase under irradiation of light to produce a water-soluble organic oxide, and transferring the water-soluble organic oxide to a water phase which forms a layer in contact with said organic solvent phase.

9 Claims, No Drawings

PROCESS FOR PREPARING WATER-SOLUBLE ORGANIC OXIDE

BACKGROUND OF THE INVENTION

1. Field of the Invention

The present invention relates to a process for preparing a water-soluble organic oxide which is useful as a raw material for various chemicals and, more particularly, to an industrially advantageous process for preparing a water-soluble organic oxide, such as 5-amino-4-oxo-2-pentenoic acid, using inexpensive molecular oxygen as an oxidizer and recycling the sensitizer used in the reaction.

2. Description of the Background Art

Oxidation reactions using singlet oxygen, wherein molecular oxygen is reacted in the presence of a sensitizer under irradiation of light, are important reactions in processes for manufacturing chemical products because of the excellent reactivity and selectivity and abundant availability of the molecular oxygen from atmosphere. Included in these reactions are an $O_2$ addition reaction using high energy singlet state oxygen molecule produced by energy from a sensitizer which has been excited by irradiation of light, an oxidation reaction involving secondary decomposition of $O_2$ adducts, and the like. Given as a specific example of the process using such an oxidation reaction is a process for preparing an N-protected 5-amino-4-oxo-2-pentenoic acid, a raw material for the synthesis 5-aminolevulinic acid which is useful as various chemicals, a herbicide, and the like. According to this process, an N-protected 5-amino-4-oxo-2-pentenoic acid can be prepared by reacting furfurylamine, of which the amino group has been protected, with oxygen molecule under irradiation by light in the presence of a sensitizer in pyridine (U.S. Pat. No. 5,380,935).

Because the oxidation reaction with singlet oxygen has been conventionally carried out in a system wherein the raw material and a sensitizer are homogeneously dissolved in a solvent, the reaction product is obtained as a mixture with the sensitizer in the solvent and it was difficult to isolate the reaction product from the mixture. Furthermore, because a sensitizer generally absorbs visible lights, it conspicuously dyes the products if contained in the products even in a trace amount. A step of removing the sensitizer after the reaction was thus required for obtaining a high purity product.

A method of adsorbing the sensitizer in activated carbon and separating out the activated carbon is a most commonly used method for the removal of the sensitizer from the oxidation reaction products. According to this method, not only it takes a long period of time for the sensitizer to be adsorbed in activated carbon, but also it is difficult to completely remove the sensitizer. In addition, because the sensitizer adsorbed in activated carbon and the activated carbon used for the adsorption cannot be regenerated for reuse, it is difficult to continuously carry out the oxidation reaction. This gives rise to a high production cost of the organic oxides.

As a means for overcoming this problem, a method of using the sensitizer carried on a carrier such as an ion-exchange resin has been proposed. The sensitizer carried on a carrier, however, exhibits only low efficiencies in both irradiation by light and oxygen activation. The method was thus not practical.

SUMMARY OF THE INVENTION

In view of this situation, the present inventors have undertaken extensive studies and found that if the oxidation reaction with singlet oxygen is carried out in an organic solvent using a water-insoluble sensitizer, the reaction product (an organic oxide) can be separated from the sensitizer by transferring it to the water phase, thereby preventing the sensitizer from being incorporated in the reaction product and enabling the sensitizer to be recovered for reuse. Furthermore, the inventors have found that the process can be made continuous by successively carrying out the oxidation reaction by removing the water layer and adding fresh water and a raw material to the system. These findings have led to the completion of the present invention.

Accordingly, an object of the present invention is to provide a process for preparing a water-soluble organic oxide, for example an N-protected 5-amino-4-oxo-2-pentenoic acid, useful as a raw material for the synthesis 5-aminolevulinic acid, by an oxidation reaction using singlet oxygen.

This object of the present invention can be achieved by a process for preparing a water-soluble organic oxide which comprises, reacting an oil-soluble organic compound with molecular oxygen in the presence of a water-insoluble sensitizer in an organic solvent phase under irradiation of light to produce a water-soluble organic oxide, and transferring the water-soluble organic oxide to a water phase which forms a layer in contact with said organic solvent phase.

Other and further objects, features and advantages of the present invention will appear more fully from the following description.

DETAILED DESCRIPTION OF THE INVENTION AND PREFERRED EMBODIMENTS

The process of the present invention will be illustrated in detail.

In the present invention the oxidation reaction using singlet oxygen is carried out in an organic solvent phase and the reaction product is transferred to a water phase. The raw material is thus an oil-soluble compound and the product is a water-soluble compound. The following reactions are given as examples of the reaction for preparing a water-soluble organic compound from an oil-soluble organic compound.

(1) A reaction for preparing a hydroperoxide from an olefin, e.g., 2-methyl-2-hydroperoxy-3-pentene from 2-methyl-2-pentene, according to the following formula (1):

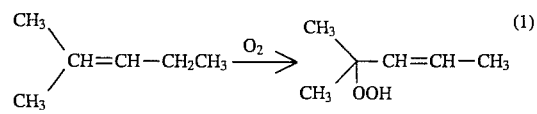

(2) A reaction for preparing 4-oxo-2-butenoic acid from a substituted furan according to the following formula (2):

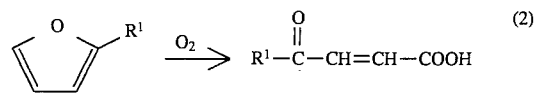

wherein $R^1$ represents an alkyl group or an N-substituted aminomethyl group.

(3) A reaction for preparing 4-hydroxy-2-butene lactam from pyrrole according to the following formula (3):

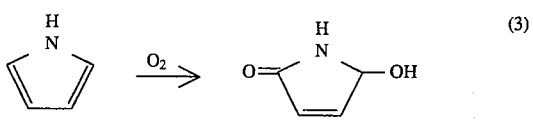

The process of the present invention can be most appropriately applied to the reaction of the above formula (2), and particularly to the reaction wherein $R^1$ is an N-substituted aminomethyl group. In the case where the $R^1$ is an N-substituted aminomethyl group, the oil-soluble organic compound is furfurylamine of which the amino group is protected and the water-soluble organic compound is 5-amino-4-oxo-2-pentenoic acid of which the amino group is protected. Although in this reaction N-protected 5-aminomethyl-5-hydroxy-2,5-dihydrofuran-2-one is produced together with N-protected 5-amino-4-oxo-2-pentenoic acid, only N-protected 5-amino-4-oxo-2-pentenoic acid is transferred to the water phase because the N-protected 5-aminomethyl-5-hydroxy-2,5-dihydrofuran-2-one is an oil-soluble compound.

The oxidation step in the process of the present invention is carried out by dissolving the raw material in an organic solvent, adding a water-insoluble sensitizer to the solution, and bubbling molecular oxygen into the mixture under irradiation of light. The water-soluble organic oxide obtained by the oxidation reaction in the organic solvent phase is then transferred to a water layer to separate it from the raw material and the sensitizer. In this instance, the water layer may be formed by adding water after the oxidation reaction is completed in the organic solvent phase to transfer the resulting water-soluble organic oxide thereto, or it is possible to carry out the oxidation reaction in a two-layer liquid system consisting of an organic solvent layer and a water layer, wherein the water-soluble organic oxide produced in the organic solvent layer is slowly transferred to the water layer.

For the purpose of bringing the organic solvent layer to come contact directly with the water layer, the use of an organic solvent possessing low water solubility is preferred in the present invention. Examples of such organic solvents include hydrocarbon solvents such as toluene, benzene, xylene and hexane; esters of fatty acid such as ethyl acetate and methyl acetate; halogen-containing solvent such as chloroform and dichloromethane; and ethers such as diethyl ether. Of these, benzene, toluene and ethyl acetate are particularly preferred.

The amount of the organic solvent used is preferably 50–0.5 ml, particularly preferably 10–1 ml, per 1 mmol of the raw material.

Although there are no specific limitations to the proportion of the organic solvent and water used in the oxidation reaction, the water-soluble organic oxide, which is the reaction product, may remain in the organic solvent layer if the amount of water is too small; if the amount of water is too large, on the other hand, the efficiency of irradiation of light to the organic solvent layer is lowered. Generally, the ratio by volume of the water layer and the organic layer is 1:9 to 9:1, and preferably 3:7 to 7:3.

An organic basic solvent, such as pyridine, may be present when it is needed depending on the type of raw material oil-soluble organic compound, to the extent that the interface of the two layers does not disappear. In this instance, although the amount of the organic basic solvent used is varied depending on the proportion of the water and the organic solvent, typically an amount not more than 75 ml of the organic basic solvent is used for a solvent system consisting of 75 ml of toluene and 75 ml of water.

Water-insoluble sensitizers having a high oil solubility is preferably used in the present invention. Specific examples of such sensitizers include condensed polycyclic aromatic compounds such as benzophenone, coronene and fullerene.

The sensitizer can be used at a concentration of $10^{-1}$–$10^{-5}$ mol/l in the organic solvent, with the concentration of $10^{-2}$–$10^{-4}$ mol/l being preferred in view of the reaction efficiency and the like.

Molecular oxygen used as the oxidizer can be oxygen in the air or commercially available oxygen gas. Oxygen atom or ozone is excluded. The molecular oxygen may be used diluted with an inert gas such as nitrogen.

The amount of oxygen gas supplied can be suitably determined depending on the concentration of oxygen in the gas, the amount of the solvent, the concentration of the raw material, and the reaction temperature. For instance, when the oxygen gas is fed at room temperature to a reaction system containing 0.2 mmol of the water-insoluble sensitizer for 10 mmol of the raw material, a preferable feed rate of the oxygen gas is 5–50 ml/min for 100 ml of the reaction mixture. Although the feed rate of oxygen should be sufficient enough to make up for the oxygen consumed in the reaction, an excessive amount of oxygen is unnecessary and too small an amount cannot cause the reaction to proceed. When the reaction is carried out under the atmosphere of pure oxygen, recycle of the vapor phase or the vapor-phase tangling method by agitation may be adopted instead of bubbling of oxygen.

There are no specific limitations as to the source of the light used for irradiation. Any optional sources, such as sunlight, fluorescent lamp, high-pressure mercury lamp and tungsten-halogen lamp, can be used. Among these, especially preferred are fluorescent lamp, tungsten-halogen lamp, and high-pressure mercury lamp, because of the high energy efficiency of visible lights.

A reaction temperature as low as possible is preferred for stabilizing singlet oxygen. Specifically, on the condition that the solvent is not solidified, a temperature not more than 50° C., preferably not more than 20° C., and more preferably 10° C. to −5° C., can be employed. The reaction is normally completed within 2–6 hours at a temperature in these ranges.

It is desirable that the reaction be carried out under the normal pressure (the atmospheric pressure). Under reduced pressure the amount of dissolved oxygen is decreased, which gives rise to a retarded reaction rate. On the other hand, when the reaction is carried out under pressure, the two-molecule deactivation of singlet oxygen may occur even if the amount of dissolved oxygen is increased by raising the pressure.

When N-protected furfurylamine is oxidized by the process of the present invention, an organic solvent in an amount of 2–20 ml is preferably used for 1 mmol of the N-protected furfurylamine. When an organic basic solvent is present in the organic solvent layer, the amount of the organic basic solvent may be 1–30 ml, while using 1–10 mg of water insoluble sensitizer. It is desirable that the ratio by volume of water and the organic solvent be 1:9–5:5, or 1.5:8.5–5:5 when the organic solvent is ethyl acetate which has a comparatively high solubility in water. The reaction temperature may be −5° to 25° C., especially preferably −5° to 10° C.

For example, when the reaction is carried out using 10 mmol of N-protected furfurylphthalimide, 75 ml of toluene, 75 ml of water, 20 ml of pyridine and 50 mg of coronene at a temperature of 10° C., N-protected 5-amino-4-oxo-2-pentenoic acid can be produced as an aqueous solution by bubbling oxygen at a rate of 10–200 ml/min under irradiation of light. Crystals of N-protected 5-amino-4-oxo-2-pentenoic acid can then be obtained by concentrating this aqueous solution to dryness under reduced pressure.

According to the process of the present invention, inclusion of the sensitizer in the product obtained by the oxidation reaction using singlet oxygen can be avoided, and the sensitizer can be reused for the successive reactions. For example, N-protected 5-amino-4-oxo-2-pentenoic acid, which is useful as a raw material for the manufacture of 5-aminolevulinic acid, can be prepared at a high yield and a high purity.

Japanese Patent Application No. 23887/1994 filed on Feb. 22, 1994 is hereby incorporated by reference.

Other features of the invention will become apparent in the course of the following description of the exemplary embodiments which are given for illustration of the invention and are not intended to be limiting thereof.

EXAMPLES

Example 1

2.27 g (10.0 mmol) of N-furfurylphthalimide and 50 mg of coronene were charged to a 200 ml three-necked glass flask equipped with an oxygen feed tube, a thermometer, and a lamp protector tube with a water-cooling jacket. The mixture was dissolved in 75 ml of toluene. After the addition of 75 ml of water and 30 ml of pyridine, oxygen gas was fed at a rate of 20 ml/min at 10°–20° C. while irradiating light from inside the flask. A 100 W tungsten-halogen lamp was used as a light source.

After 6 hour irradiation, the aqueous layer was separated and concentrated to dryness under reduced pressure. 2.56 g (yield 76%) of light brown solid was obtained as an oxidation product.

Spectrum data of this oxidation product are as follows. Based on the spectrum data, it was confirmed that this product was pyridine salt of 4-oxo-5-phthalimido-2-pentenoic acid.

$^1$H-NMR (δ ppm in D$_2$O, 400 MHz): 4.80(2H, s), 6.84(1H, d), 7.13(1H, d), 7.30–8.20(Ar 7H, m), 8.53–8.61(Ar 2H, m)

IR cm$^{-1}$ (Nujor method): 1770, 1710, 1630, 1480, 1470, 1420, 1380, 1310, 1195, 1110, 1090, 980, 950, 720, 690, 610, 535

Example 2

The same experiment as in Example 1 was carried out, except for using 10 mg of fullerene (C$_{60}$) instead of 50 mg of coronene, to obtain 2.61 g (yield 77%) of light brown crystals of pyridine salt of 4-oxo-5-phthalimido-2-pentenoic acid.

Examples 3–11

75 ml of water, 20 ml of pyridine, and 2.27 g (10.0 mmol) of N-furfurylphthalimide were added to the toluene layer (the reaction mixture remaining after separation of the water layer) of Example 1. Oxygen gas was fed at a rate of 20 ml/min at 10°–15° C. under irradiation of light using the same apparatus as in Example 1.

After 6 hours, the aqueous layer was separated and concentrated to dryness under reduced pressure to obtain 2.57 g (yield 76%) of light brown solid of pyridine salt of 4-oxo-5-phthalimido-2-pentenoic acid was obtained (Example 3).

The same amounts of water, pyridine and furfurylphthalimide as in Example 3 were added to the organic layer obtained after separation of the water layer in Example 3. The same procedure as in Example 1, from irradiation of light through concentration to dryness, was carried out to obtain pyridine salt of 4-oxo-5-phthalimido-2-pentenoic acid (Example 4). Pyridine salt of 4-oxo-5-phthalimido-2-pentenoic acid was repeatedly prepared by repeatedly using the organic layer instead of toluene and the sensitizer in the same manner as Examples 3 (Examples 5–11).

The yield, purity, color and form of pyridine salt of 4-oxo-5-phthalimido-2-pentenoic acid prepared in these Examples are shown in Table 1, wherein is shown that the same pyridine salt of 4-oxo-5-phthalimido-2-pentenoic acid as in Examples 1 and 3 can be obtained by the repeated use of the sensitizer.

TABLE 1

| Example | Reaction time (hour) | Yield (g) | Yield (%) | Color/Form |
|---------|---------------------|-----------|-----------|------------|
| 3       | 6                   | 2.57      | 76        | Light brown crystals |
| 4       | 6                   | 2.80      | 83        | Light brown crystals |
| 5       | 6                   | 2.80      | 83        | Light brown crystals |
| 6       | 6                   | 3.01      | 89        | Light brown crystals |
| 7       | 6                   | 3.10      | 92        | Light brown crystals |
| 8       | 6                   | 2.69      | 80        | Light brown crystals |
| 9       | 6                   | 3.06      | 91        | Light brown crystals |
| 10      | 6                   | 3.19      | 94        | Light brown crystals |
| 11      | 6                   | 3.07      | 91        | Light brown crystals |

Example 12

1.07 ml (10.0 mmol) of 2,5-dimethylfuran, 3.15 g (12.0 mmol) of triphenylphosphine and 5 mg of fullerene (C$_{60}$) were charged to a 200 ml three-necked glass flask equipped with an oxygen feed tube, a thermometer, and a lamp protector tube with a water-cooling jacket. The mixture was dissolved in 70 ml of toluene. After the addition of 70 ml of water, oxygen gas was fed at a rate of 40 ml/min at 10°–20° C. while irradiating light from inside the flask. A 250 W tungsten-halogen lamp was used as a light source.

After 1 hour irradiation, the aqueous layer was separated and concentrated to dryness under reduced pressure. 890.3 mg of light yellow solid was obtained. As a result of analysis by gas chromatography, the crystals were confirmed to be 3-hexene-2,5-dione containing a slight amount of triphenylphosphine oxide. The crystals were dissolved in 30 ml of ether to separate insoluble matters by filtration, and the filtrate was concentrated to dryness under reduced pressure to obtain 879 mg (yield 78%) of white crystals of 3-hexene-2,5-dione.

Comparative Example 1

1.07 ml (10.0 mmol) of 2,5-dimethylfuran, 3.15 g (12.0 mmol) of triphenylphosphine and 6 mg (6 μmol) of Rose Bengal were charged to the same flask as used in Example 12 and the mixture was dissolved in 150 ml of methanol.

Oxygen gas was fed at a rate of 40 ml/min at 10°–20° C. while irradiating light from inside the flask. A 250 W tungsten-halogen lamp was used as a light source.

After 1 hour irradiation, the reaction mixture was analyzed to confirm that it is a mixture of 3-hexene-2,5-dione, triphenylphosphine oxide, triphenylphosphine, and 2,5-dimethylfuran.

This Comparative Example is given to show the reaction using only an organic phase. It was impossible to isolate the target compound by this method.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing a water-soluble organic oxide which comprises, reacting an oil-soluble organic compound with molecular oxygen in the presence of a water-insoluble sensitizer in one or a mixture of organic solvents under irradiation of light to produce a water-soluble organic oxide, wherein water is added before or after the reaction is completed to produce an organic solvent-containing layer and a water-containing layer and transferring the water-soluble organic oxide to the water layer.

2. The process according to claim 1, wherein said oil-soluble organic compound is an olefin and said water-soluble organic oxide is a hydroperoxide.

3. The process according to claim 1, wherein said oil-soluble organic compound is a substituted furan and said water-soluble organic oxide is 4-oxo-2-butenoic acid.

4. The process according to claim 1, wherein said oil-soluble organic compound is pyrrole and said water-soluble organic oxide is 4-hydroxy-2-butene lactam.

5. The process according to claim 1, wherein said oil-soluble organic compound is furfurylamine of which the amino group is protected and said water-soluble organic oxide is 5-amino-4-oxo-2-pentenoic acid of which the amino group is protected.

6. The process according to claim 1, wherein said organic solvent is one or more solvents selected from the group consisting of hydrocarbon solvents, fatty acid esters, halogen-containing solvents and ethers.

7. The process according to claim 1, wherein the organic solvent is selected from the group consisting of toluene, xylene, benzene, hexane, ethyl acetate, methyl acetate, chloroform, dichloromethane, diethyl ether, and a mixture thereof.

8. The process according to claim 1, wherein said sensitizer is a condensed polycyclic aromatic compound.

9. The process according to claim 1, wherein said sensitizer is a benzophenone, coronene or fullerene.

* * * * *